(12) United States Patent
Dunne (10) Patent No.: US 8,677,825 B1
(45) Date of Patent: Mar. 25, 2014

(54) IDENTIFICATION OF LAMB WAVE MODES

(75) Inventor: James P. Dunne, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 306 days.

(21) Appl. No.: 13/172,380

(22) Filed: Jun. 29, 2011

(51) Int. Cl.
 *G01N 29/032* (2006.01)

(52) U.S. Cl.
 USPC .............................................. 73/587; 73/599

(58) Field of Classification Search
 USPC ............ 73/587, 579, 597, 598, 600, 602, 599
 See application file for complete search history.

(56) References Cited

U.S. PATENT DOCUMENTS

| | | | | |
|---|---|---|---|---|
| 6,182,512 B1 * | 2/2001 | Lorraine | ......................... | 73/655 |
| 7,117,742 B2 * | 10/2006 | Kim | ................................ | 73/587 |
| 7,376,519 B2 * | 5/2008 | Morin et al. | ..................... | 702/35 |
| 7,536,912 B2 * | 5/2009 | Kim | ................................ | 73/632 |
| 7,590,510 B2 * | 9/2009 | Kim | ............................. | 702/183 |
| 7,596,470 B2 * | 9/2009 | Kim | ............................. | 702/183 |
| 7,660,690 B2 * | 2/2010 | Gordon et al. | ................. | 702/116 |
| 7,783,433 B2 * | 8/2010 | Gordon et al. | ................. | 702/39 |
| 7,891,247 B2 | 2/2011 | Ihn | | |
| 8,015,877 B2 * | 9/2011 | Ihn | ................................. | 73/603 |
| 8,225,665 B2 * | 7/2012 | Geir et al. | ....................... | 73/597 |
| 2003/0167141 A1 * | 9/2003 | Staszewski | ..................... | 702/77 |
| 2009/0032329 A1 | 2/2009 | Ihn | | |

FOREIGN PATENT DOCUMENTS

DE          10041711     *  3/2002

OTHER PUBLICATIONS

Lee, Changgil, et al., The effect of through-the-thickness holes on a reference-free damage diagnosis technique.

* cited by examiner

*Primary Examiner* — J M Saint Surin
(74) *Attorney, Agent, or Firm* — Charles L. Moore; Moore & Van Allen PLLC (57) ABSTRACT

A method for identifying Lamb wave modes and structural health monitoring may include transmitting a Lamb wave through a structure for monitoring the structural health of the structure. The method may also include measuring an instantaneous thickness of the structure at a predetermined location of the structure during passage of the Lamb wave at the predetermined location. The method may additionally include identifying a mode of the Lamb wave from the instantaneous thickness of the structure.

20 Claims, 5 Drawing Sheets

IDENTIFICATION OF LAMB WAVE MODES

BACKGROUND

The present disclosure relates to detecting anomalies, defects or damage in a structure or structural health monitoring of a structure, such as an aircraft, civil structure or other structure, and more particularly to a method and system for identifying the mode of a Lamb wave being transmitted through the structure for structural health monitoring or detecting anomalies.

Determining the particular mode of a Lamb wave being propagated or transmitted through a structure to monitor the structural health of the structure or to detect any anomalies using direct measurement techniques typically involves placing two piezoelectric transducers on the structure. The transducers must be on opposite sides of the structure being monitored or evaluated. Additionally, the transducers have to be exactly opposite one another to accurately measure the phase of the Lamb wave during passage of the Lamb wave through the structure at the location flanked by the opposing transducers. By observing the response of each of the transducers, a determination can be made about whether the wave sensed on each side is either in-phase, which indicates the symmetric (S0) mode, or out-of-phase, which indicates the asymmetric (A0) mode. This method or technique may be prohibitive in some structural health monitoring (SHM) applications. For example, it may not be possible to place transducers on both sides of a structure or exactly opposite one another. This technique also requires additional transducers, wiring and electronics resulting in additional cost and complexity of the system.

BRIEF SUMMARY

According to one aspect of the present disclosure, a method for identifying Lamb wave modes and structural health monitoring may include transmitting a Lamb wave through a structure for monitoring the structural health of the structure. The method may also include measuring an instantaneous thickness of the structure at a predetermined location of the structure during passage of the Lamb wave at the predetermined location. The method may additionally include identifying a mode of the Lamb wave from the instantaneous thickness of the structure.

According to one aspect of the present disclosure, a method for identifying Lamb wave modes and structural health monitoring may include transmitting a Lamb wave through a structure for monitoring the structural health of the structure. The method may also include measuring an instantaneous thickness of the structure at a predetermined location of the structure during passage of the Lamb wave at the predetermined location using a single transducer mounted on only one side of the structure. The method may additionally include measuring wave propagation characteristics of the traveling Lamb wave using the transducer. The method may further include identifying a mode of the Lamb wave from the instantaneous thickness of the structure.

According to another aspect of the present disclosure, a system for identifying Lamb wave modes and structural health monitoring may include a mechanism for measuring an instantaneous thickness of a structure at a predetermined location of the structure during passage of a Lamb wave at the predetermined location, wherein the mechanism is attached to one side of the structure. The system may also include a module for identifying a mode of the Lamb wave from the instantaneous thickness of the structure.

BRIEF DESCRIPTION OF THE SEVERAL VIEWS OF THE DRAWINGS

The present disclosure is further described in the detailed description which follows in reference to the noted plurality of drawings by way of non-limiting examples of embodiments of the present disclosure in which like reference numerals represent similar parts throughout the several views of the drawings and wherein.

DETAILED DESCRIPTION

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
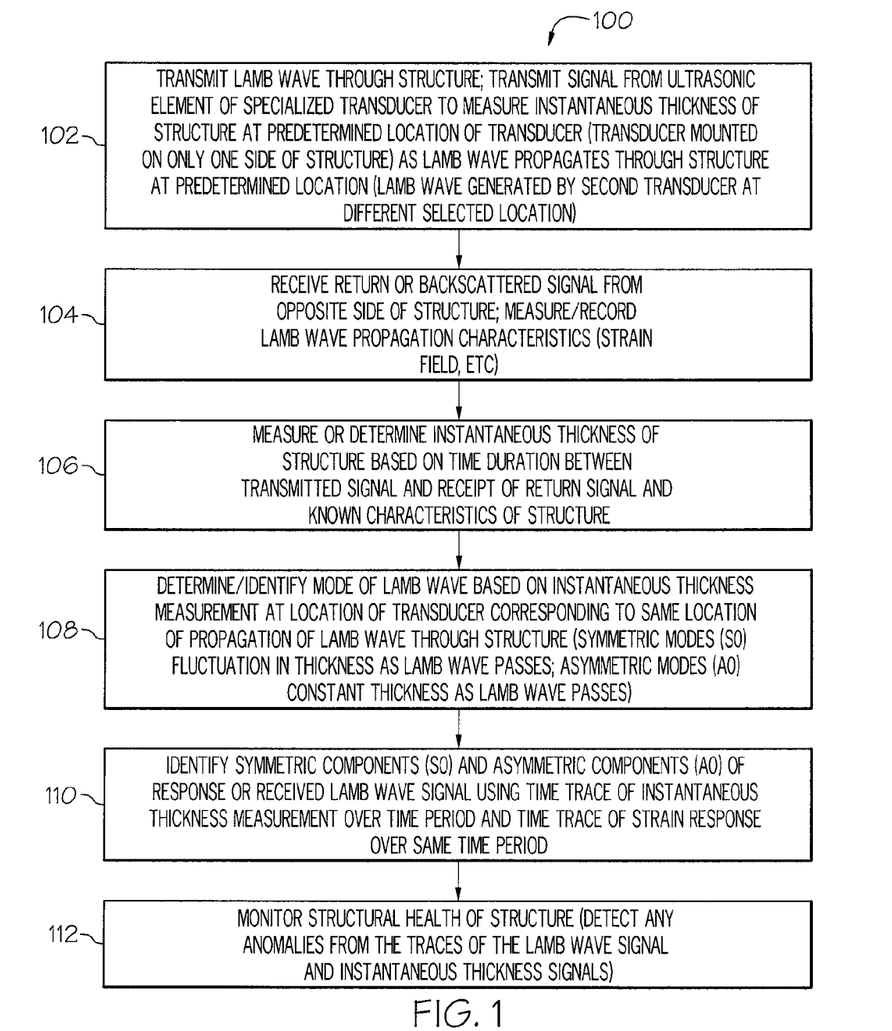
FIG. 1 is a flow chart of an example of a method for identifying Lamb wave modes in accordance with an embodiment of the present disclosure.

FIG. 1 is a flow chart of an example of a method 100 for identifying Lamb wave modes in accordance with an embodiment of the present disclosure. In block 102, a Lamb wave may be transmitted or propagated through a structure for monitoring the structural health of the structure or for detecting any anomalies, damage or defects in the structure. The structure may be a metallic material, composite material, laminated material or other construction. The structure may be part of an aircraft, civil structure or other structure in which monitoring the structural health or detecting flaws may be desired.

Also in block 102, a signal may be transmitted into the structure to measure an instantaneous thickness of the structure at a predetermined location of the structure during passage of the Lamb wave through the structure at the predetermined location. The signal may be transmitted orthogonally or normal to a surface of one side of the structure so that the signal is returned or scattered by a directly opposite side of the structure as described herein for measuring the instantaneous thickness of the structure and for determining a mode of the Lamb wave. Accordingly, only a single transducer or device is needed for measuring the thickness of the structure for identifying the mode of the Lamb wave. The signal may be an ultrasound signal or similar signal for measuring the instantaneous thickness of the structure. The ultrasound signal may be transmitted by an ultrasound element of a specialized transducer. An example of a specialized transducer that may be used for transmitting the signal for measuring the instantaneous thickness will be described in more detail with reference to FIG. 2. The specialized transducer is mounted on only one side of the structure thus eliminating the need for a second transducer on an opposite side of the structure and the additional wiring connections associated therewith. The Lamb wave may be generated by a second transducer or other Lamb wave generating element at a different selected location on the structure.

In block 104, a return signal or backscattered signal scattered by an opposite side of the structure may be received or detected. The return signal may be received by the specialized transducer that transmitted the original signal or the return signal may be received or detected by a separate transducer.

Also in block 104, propagation characteristics of the traveling Lamb wave, such as a strain field and other characteristics, may be measured and recorded. The specialized transducer may include a mechanism for detecting and measuring the propagation characteristics of the Lamb wave. Alternatively, another transducer may detect and measure the characteristics of the traveling Lamb wave.

In block 106, the instantaneous thickness of the structure at the predetermined or selected location may be measured or determined. The instantaneous thickness of the structure may be calculated based on a time duration between the transmitted signal and receipt of the return or backscattered signal from the opposite side of the structure and taking into account any known characteristics of the structure, such as the types of materials, construction or assembly of the materials and similar characteristics.

Figure 4A:
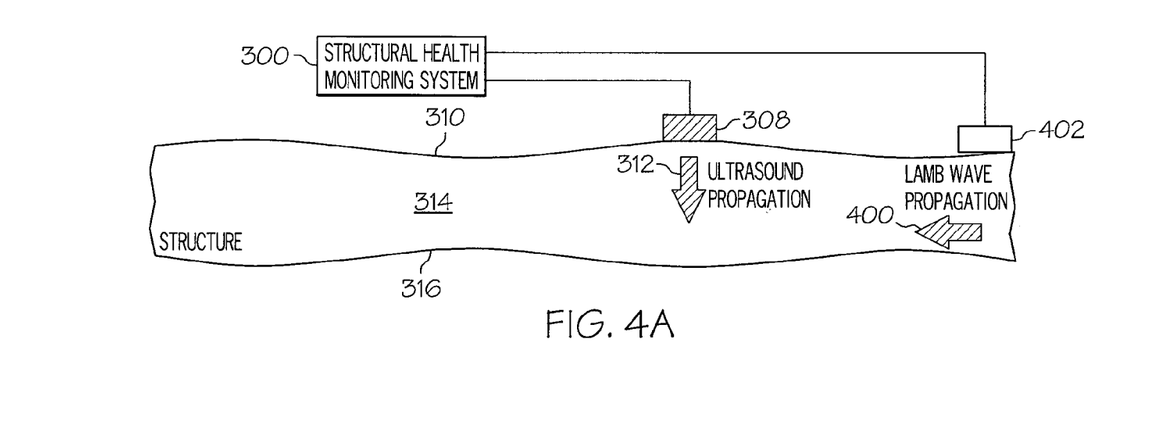
FIGS. 4A and 4B are an illustration of a Lamb wave with a symmetric (S0) mode characteristic propagating through the structure in accordance with an embodiment of the present disclosure.
Figure 4B:
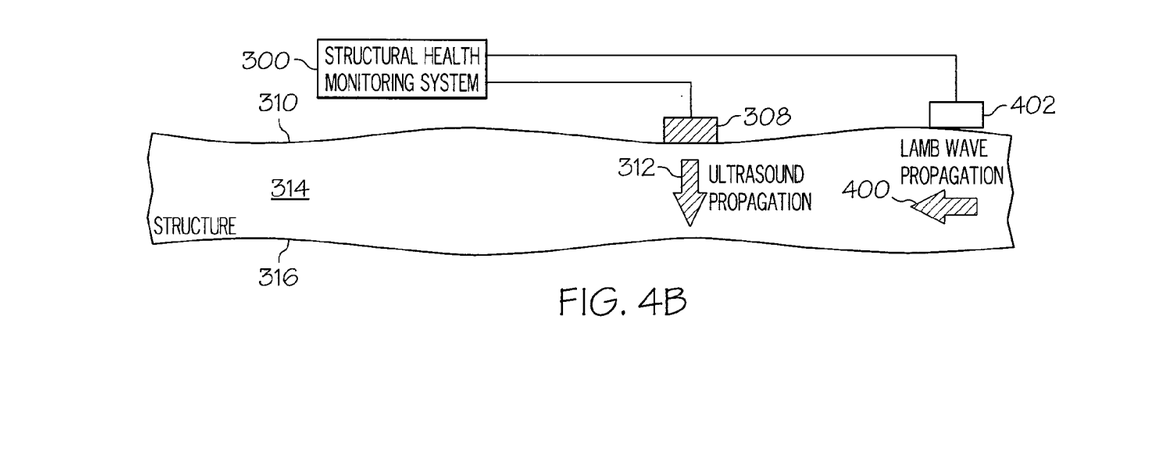

In block 108, a mode of the Lamb wave may be determined or identified based on the instantaneous thickness of the structure at the predetermined location or location of the transducer during passage of the Lamb wave at the predetermined location. Symmetric modes (S0) and asymmetric modes (A0) of the traveling Lamb wave may be identified or determined from the instantaneous thickness measurement of the structure. For symmetric modes of the Lamb wave, the instantaneous thickness of the structure at the predetermined location will fluctuate or alternate between an increased thickness and a decreased thickness as the Lamb wave passes. An example of a symmetric mode Lamb wave where measurement of the instantaneous thickness fluctuates between increased and decreased thicknesses at the predetermined location is illustrated in FIGS. 4A and 4B. The effects of the Lamb waves on the structure are illustrated in FIGS. 4A and 4B as being exaggerated or at a high level of magnification in order to illustrate the fluctuation of the instantaneous thickness of the structure caused by the symmetric mode Lamb waves.

Figure 5A:
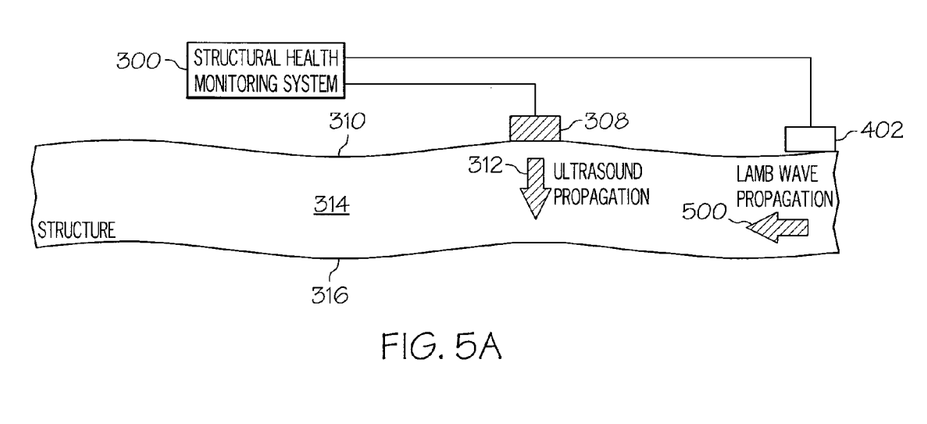
FIGS. 5A and 5B are an illustration of a Lamb wave with an asymmetric (A0) mode characteristic propagating through the structure in accordance with an embodiment of the present disclosure.
Figure 5B:
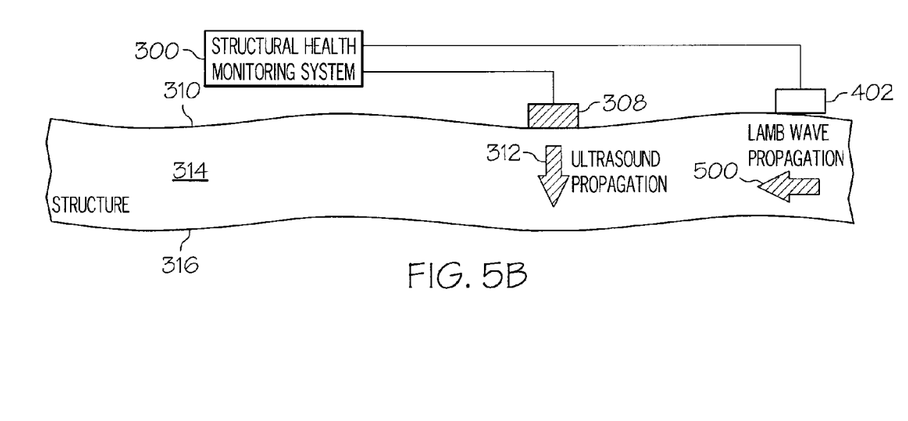

For asymmetric modes of the Lamb wave, the instantaneous thickness of the structure at the predetermined location of the transducer will be a constant thickness as the Lamb wave passes the predetermined location. An example of an asymmetric mode of the Lamb wave where measurement of the instantaneous thickness is constant as the Lamb wave passes is illustrated in FIGS. 5A and 5B. The effects of the Lamb waves on the structure are also illustrated in FIGS. 5A and 5B as being exaggerated or at a high level of magnification in order to illustrate the constant instantaneous thickness of the structure under influence of asymmetric mode Lamb waves.

Figure 4C:
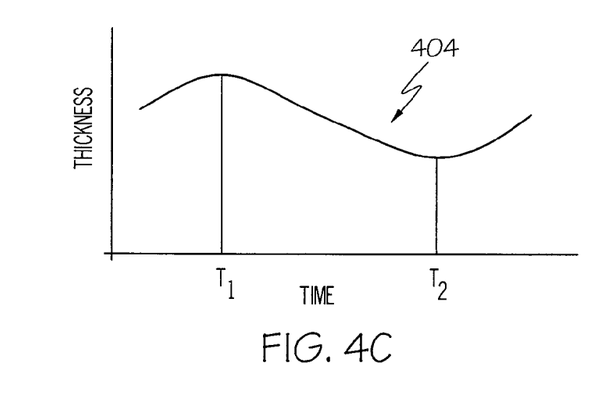
FIG. 4C is an example of an instantaneous thickness measurement of the structure or trace over a predetermined time period during propagation of the symmetric (S0) mode Lamb wave in FIGS. 4A and 4B in accordance with an embodiment of the present disclosure.
Figure 5C:
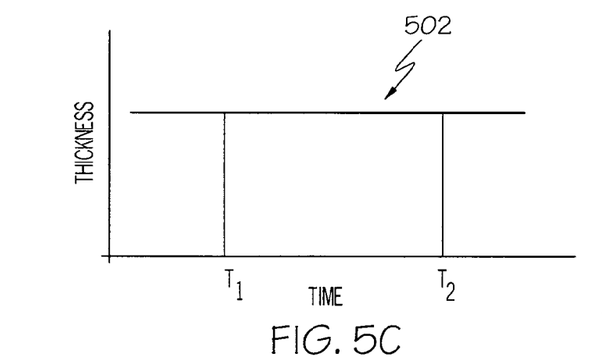
FIG. 5C is an example of an instantaneous thickness measurement of the structure or trace over a predetermined time period during propagation of the asymmetric (A0) mode Lamb wave in FIGS. 5A and 5B in accordance with an embodiment of the present disclosure.

In block 110, symmetric components (S0) and asymmetric components (A0) of the response or received Lamb wave signals may be identified or determined using a time trace of the instantaneous thickness measurement over a selected time period and a time trace of the Lamb wave propagation characteristics or strain response over the same time period. Examples of the time trace of the instantaneous thickness measurements for the symmetric Lamb wave mode and the asymmetric Lamb wave mode are illustrated in FIGS. 4C and 5C, respectively.

In block 112, the structural health of the structure may be monitored by detecting any anomalies from the traces of the Lamb wave signal and the instantaneous thickness signals taking into account the mode of the Lamb waves.

Figure 2:
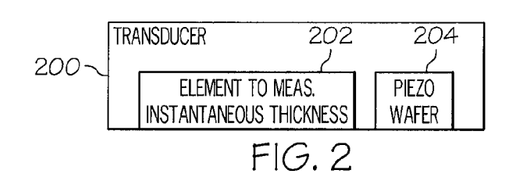
FIG. 2 is a block schematic diagram of an example of a specialized transducer for measuring instantaneous thickness of a structure and Lamb wave propagation characteristics in accordance with an embodiment of the present disclosure.

FIG. 2 is a block schematic diagram of an example of a specialized transducer 200 that may be used for measuring instantaneous thickness of a structure and Lamb wave propagation characteristics in accordance with an embodiment of the present disclosure. The specialized transducer 200 may be used to perform the operations described in the method 100 in FIG. 1. The specialized transducer 200 may include an element to measure the instantaneous thickness 202 of a structure being monitored or tested for any anomalies, damage or defects. The element to measure instantaneous thickness 202 may be an ultrasound element or generator to transmit an ultrasound signal perpendicular or normal to a surface of a structure on which the transducer 200 is mounted. The element 202 may also receive a return or scattered signal from an opposite side of the structure being monitored. Alternatively, the transducer 200 may include a separate element (not shown in FIG. 2 for purposes of clarity) for receiving the return signal.

The specialized transducer 200 may also include a piezo wafer 204 or similar component capable of receiving and detecting propagation characteristics of the traveling Lamb waves, such as the strain field or other characteristics useful in monitoring the structural health of the structure or detecting anomalies in the structure.

Figure 3A:
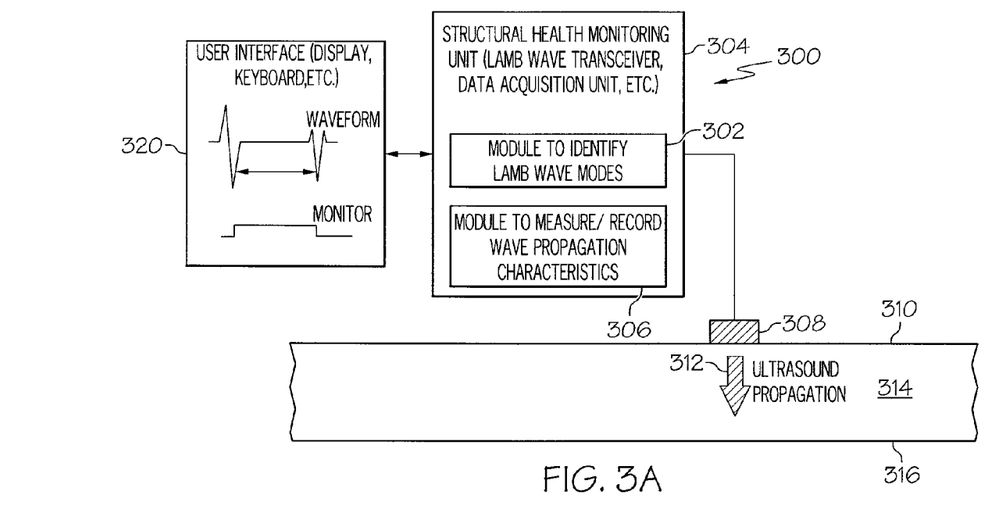
FIG. 3A is a block schematic diagram of an example of a structural health monitoring system including a module to identify Lamb wave modes in accordance with an embodiment of the present disclosure.

FIG. 3A is a block schematic diagram of an example of a structural health monitoring system 300 including a module 302 to identify Lamb wave modes in accordance with an embodiment of the present disclosure. The structural health monitoring system 300 may include a structural health monitoring unit 304. The structural health monitoring unit 304 may include a Lamb wave transceiver data acquisition unit and other components for monitoring the structural heath of a structure. The module 302 to identify Lamb wave modes may be embodied in the structural health monitoring unit 304. The structural health monitoring unit 304 may also include a module 306 to measure and record wave propagation characteristics of the traveling Lamb waves.

Figure 3B:
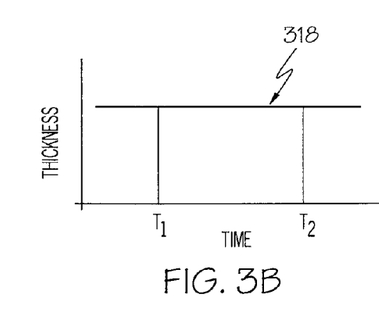
FIG. 3B is an example of an instantaneous thickness measurement of the structure in FIG. 3A over a predetermined time period in accordance with an embodiment of the present disclosure.

The structural health monitoring unit 304 may be connected to a transducer 308. The transducer 308 may be mounted on one side 310 of a structure 314. The transducer 308 may be the same or similar to transducer 200 in FIG. 2. The transducer 308 may include components for transmitting an ultrasound signal 312 into the structure 314 and for receiving the return or scattered signal from an opposite side 316 of the structure 314 to measure an instantaneous thickness of the structure 314. Without a Lamb wave propagating or traveling through the structure 314, the thickness of the structure 314 will be constant. FIG. 3B is an example of a trace 318 of the instantaneous thickness measurement of the structure 314 over a predetermined time period between times $T_1$ and $T_2$ without a Lamb wave propagating through the structure 314.

The system 300 may also include a user interface 320. The user interface 320 may include a display, a keyboard and other elements to permit a user to interface with and control the system 300 and structural health monitoring unit 304. Traces of the instantaneous thickness, such as trace 318, and responses to the propagating Lamb wave detected or measured by the transducer 308 may be presented on the display of the user interface 320.

FIGS. 4A and 4B are an illustration of a Lamb wave 400 with a symmetric (S0) mode characteristic propagating through the structure 314 in accordance with an embodiment of the present disclosure. The structure 314 may be the same as the structure 314 in FIG. 3A. The structural health monitoring system 300 may be the same as the structural health monitoring system 300 in FIG. 3A. The Lamb wave 400 may be generated by a transducer 402 or other component capable of generating the Lamb wave 400. As illustrated in FIGS. 4A and 4B, the instantaneous thickness of the structure 314 may fluctuate or alternately increase and decrease in thickness at any predetermined or selected location as the symmetric (S0) mode Lamb wave 400 propagates or travels through the structure 314. FIG. 4C is an example of the instantaneous thickness measurement of the structure 314 or trace 404 at the predetermined location of the transducer 308 over a predetermined time period between $T_1$ and $T_2$ during propagation of the symmetric (S0) mode Lamb wave 400 in FIGS. 4A and 4B. By comparing FIGS. 4A and 4B, the structure 314 is thicker at the predetermined location of the transducer 308 at time $T_1$ than in at time $T_2$ in FIG. 4B. This fluctuation or variation in the instantaneous thickness of the structure 314 at the location of the transducer 308 caused by the symmetric mode of the Lamb wave 400 is illustrated by the trace 404 or waveform in FIG. 4C.

FIGS. 5A and 5B are an illustration of a Lamb wave 500 with an asymmetric (A0) mode characteristic propagating through the structure 314 in accordance with an embodiment of the present disclosure. As illustrated in FIGS. 5A and 5B, the instantaneous thickness of the structure 314 will be constant as the asymmetric (A0) mode Lamb wave 500 propagates or travels through the structure 314. While the Lamb wave 500 causes the structure to be wavy, the asymmetric nature of the wave causes the instantaneous thickness of the structure to be constant or the same at any given location including the selected location of the transducer 308 as the Lamb wave propagates through the structure 314 over the time period. A comparison of the instantaneous thickness of the structure 314 in FIG. 5A at time $T_1$ to the instantaneous thickness of the structure 314 in FIG. 5B at $T_2$ will show that the thickness is the same or constant for the asymmetric mode Lamb wave 500. FIG. 5C is an example of an instantaneous thickness measurement of the structure or trace 502 over a predetermined time period between $T_1$ and $T_2$ during propagation of the asymmetric (A0) mode Lamb wave in FIGS. 5A and 5B. As illustrated in FIG. 5C, the thickness of the structure 314 is constant at the location of the transducer 308 over the predetermined time period. Accordingly, a mode of the Lamb wave may be determined from measurement or traces of the instantaneous thickness at a predetermined or selected location of the transducer on the structure during passage of the Lamb wave. With a time trace of the instantaneous thickness and a time trace of the strain response, the symmetric (S0) and asymmetric (A0) modes or components of the Lamb wave response may be identified or determined. This information may then be used in detecting anomalies, defects or damage, in algorithms for determining the size and shape of anomalies, defects or damage, or other structural health monitoring procedures to provide more accurate results. An example of a method and system for detecting anomalies and determining the size of such anomalies is described and claimed in U.S. Pat. No. 7,891,247, entitled "Method and System for Detecting an Anomaly and Determining Its Size," by Jeong-Beom Ihn, issued Feb. 22, 2011, and assigned to the same assignee as the present application, and which is incorporated herein in its entirety by reference. Another example of a method and system for detecting and imaging anomalies, defects or damage in a structure is described and claimed in allowed U.S. patent application Ser. No. 12/103,118, entitled "Imaging an Anomaly Using Backscattered Waves," by Jeong-Beom Ihn, and assigned to the same assignee as the present application, and which is incorporated herein in its entirety by reference.

The flowcharts and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to embodiments of the disclosure in the form disclosed. Many modifications and variations will be apparent to those of ordinary skill in the art without departing from the scope and spirit of embodiments of the disclosure. The embodiment was chosen and described in order to best explain the principles of embodiments of the disclosure and the practical application, and to enable others of ordinary skill in the art to understand embodiments of the disclosure for various embodiments with various modifications as are suited to the particular use contemplated.

Although specific embodiments have been illustrated and described herein, those of ordinary skill in the art appreciate that any arrangement which is calculated to achieve the same purpose may be substituted for the specific embodiments shown and that embodiments of the disclosure have other applications in other environments. This application is intended to cover any adaptations or variations of the present disclosure. The following claims are in no way intended to limit the scope of embodiments of the disclosure to the specific embodiments described herein.

What is claimed is:

1. A method for identifying Lamb wave modes and structural health monitoring, comprising:
   transmitting a Lamb wave through a structure for monitoring the structural health of the structure;
   measuring an instantaneous thickness of the structure at a predetermined location of the structure during passage of the Lamb wave at the predetermined location; and
   identifying a mode of the Lamb wave from the instantaneous thickness of the structure.

2. The method of claim 1, further comprising measuring the instantaneous thickness of the structure using a transducer mounted on only one side of the structure.

3. The method of claim 1, wherein measuring the instantaneous thickness of the structure comprises:
   transmitting a signal from one side of the structure to an opposite side of the structure;
   detecting a return signal scattered by the opposite side of the structure; and
   measuring an elapsed time between transmission of the signal and detecting the return signal during passage of the Lamb wave at the predetermined location, the Lamb wave propagating in a direction transverse to the signal transmitted from the one side of the structure to the opposite side of the structure at the predetermined location.

4. The method of claim 3, wherein transmitting the signal comprises transmitting an ultrasound signal.

5. The method of claim 3, further comprising transmitting the signal orthogonally into the structure from the one side so that the signal is incident on a directly opposite location of the structure.

6. The method of claim 1, further comprising recording wave propagation characteristics of the traveling Lamb wave.

7. The method of claim 1, wherein identifying a mode of the Lamb wave from the instantaneous thickness comprises identifying at least one of a symmetric mode and an asymmetric mode from the instantaneous thickness measurement at the predetermined location.

8. The method of claim 7, wherein identifying the symmetric mode comprises measuring a fluctuation in instantaneous thickness of the structure at the predetermined location as the Lamb wave passes the predetermined location.

9. The method of claim 7, wherein identifying the asymmetric mode comprises measuring a constant thickness of the structure at the predetermined location as the Lamb wave passes the predetermined location.

10. The method of claim 1, further comprising detecting any anomalies in the structure from a trace of the Lamb wave and a trace of the instantaneous thickness measurement.

11. The method of claim 1, further comprising mounting a transducer to only one side of the structure for measuring the instantaneous thickness of the structure and for recording wave propagation characteristics of traveling Lamb waves.

12. The method of claim 11, wherein the structure comprises an aircraft.

13. A method for identifying Lamb wave modes as part of a structural health monitoring system, comprising:
   transmitting a Lamb wave through a structure for monitoring the structural health of the structure;
   measuring an instantaneous thickness of the structure at a predetermined location of the structure during passage of the Lamb wave at the predetermined location using a transducer mounted on only one side of the structure;
   measuring wave propagation characteristics of the traveling Lamb wave using the transducer; and
   identifying a mode of the Lamb wave from the instantaneous thickness of the structure.

14. The method of claim 13, wherein identifying a mode of the Lamb wave from the instantaneous thickness comprises identifying at least one of a symmetric mode and an asymmetric mode from the instantaneous thickness measurement at the predetermined location;
   identifying the symmetric mode comprising measuring a fluctuation in instantaneous thickness of the structure at the predetermined location as the Lamb wave passes the predetermined location; and
   identifying the asymmetric mode comprising measuring a constant thickness of the structure at the predetermined location as the Lamb wave passes the predetermined location.

15. A system for identifying Lamb wave modes and structural health monitoring, comprising:
   a mechanism for measuring an instantaneous thickness of a structure at a predetermined location of the structure during passage of a Lamb wave at the predetermined location, wherein the mechanism is on one side of the structure; and
   a module for identifying a mode of the Lamb wave from the instantaneous thickness of the structure.

16. The system of claim 15, further comprising a transducer mounted at a predetermined location on only the one side of the structure for transmitting a signal from one side of the structure to an opposite side of the structure for measuring the instantaneous thickness of the structure.

17. The system of claim 16, wherein the transducer is adapted to detect a return signal scattered by the opposite side of the structure.

18. The system of claim 17, wherein the mechanism for measuring the instantaneous thickness of the structure comprises a module for measuring an elapsed time between transmission of the signal and detecting the return signal.

19. The system of claim 16, wherein the transducer comprises:
   an element to measure the instantaneous thickness of the structure; and
   a piezo wafer to detect wave propagation characteristics of traveling Lamb waves.

20. The system of claim 15, further comprising a module to measure and record wave propagation characteristics of traveling Lamb waves.

* * * * *